United States Patent
Cizmar et al.

(10) Patent No.: US 12,411,333 B2
(45) Date of Patent: Sep. 9, 2025

(54) HYBRID OPTICAL FIBER, ENDOSCOPIC SYSTEM, AND METHOD FOR EXAMINING A SAMPLE

(71) Applicant: LEIBNIZ-INSTITUT FUR PHOTONISCHE TECHNOLOGIEN E.V., Jena (DE)

(72) Inventors: Tomas Cizmar, Weimar (DE); Yang Du, Weimar (DE); Katrin Wondraczek, Jena (DE)

(73) Assignee: LEIBNIZ-INSTITUT FUR PHOTONISCHE TECHNOLOGIEN E.V., Jena (DE)

( * ) Notice: Subject to any disclaimer, the term of this patent is extended or adjusted under 35 U.S.C. 154(b) by 0 days.

(21) Appl. No.: 18/275,090
(22) PCT Filed: Jan. 28, 2022
(86) PCT No.: PCT/EP2022/052052
§ 371 (c)(1),
(2) Date: Jul. 31, 2023
(87) PCT Pub. No.: WO2022/162147
PCT Pub. Date: Aug. 4, 2022

(65) Prior Publication Data
US 2024/0103261 A1  Mar. 28, 2024

(30) Foreign Application Priority Data
Jan. 29, 2021 (DE) ................. 10 2021 102 092.1

(51) Int. Cl.
*G02B 23/24* (2006.01)
*G02B 6/02* (2006.01)
*G02B 6/036* (2006.01)

(52) U.S. Cl.
CPC ..... *G02B 23/2469* (2013.01); *G02B 6/02042* (2013.01); *G02B 6/02047* (2013.01); *G02B 6/03633* (2013.01)

(58) Field of Classification Search
CPC ............ G02B 23/2469; G02B 6/02042; G02B 6/02047; G02B 6/03633
See application file for complete search history.

(56) References Cited

U.S. PATENT DOCUMENTS

| | | | | |
|---|---|---|---|---|
| 5,566,196 A | * | 10/1996 | Scifres | H01S 3/06708 372/6 |
| 2004/0264513 A1 | * | 12/2004 | Shima | H01S 3/06708 372/6 |

(Continued)

FOREIGN PATENT DOCUMENTS

DE  102018112253 A1  11/2019

OTHER PUBLICATIONS

International Search Report and Written Opinion mailed on May 20, 2022 for International Patent Application No. PCT/EP2022/052052 w/English Translation.

(Continued)

*Primary Examiner* — Georgia Y Epps
*Assistant Examiner* — Monica T Taba
(74) *Attorney, Agent, or Firm* — HUNTON ANDREWS KURTH LLP

(57) ABSTRACT

The invention relates to a hybrid optical fiber (1) which comprises a plurality of fiber cores (2), a first cladding (3) which encloses the plurality of fiber cores (2), and a second cladding (4) which surrounds the first cladding (3). In this case, the fiber cores (2) have a first refractive index $n_1$, the first cladding (3) has a second refractive index $n_2$ and the second cladding (4) has a third refractive index $n_3$, $n_1$ being greater than $n_2$ and $n_2$ being greater than $n_3$. Furthermore, the invention relates to an endoscopic system (8) for examining a sample (9), comprising a hybrid optical fiber (1) and an optical arrangement (21). The optical arrangement (21) comprises a coherent light source (13) for introducing light into a proximal end of the hybrid optical fiber (1), such that the fiber cores (2) of the hybrid optical fiber (1) together with the first cladding (3) of the hybrid optical fiber (1) function as a multimode optical fiber. Furthermore, the optical arrangement (21) comprises a photodetector (20), compris- (Continued)

ing a plurality of pixels, for detecting the light exiting the individual fiber cores (2). The invention also relates to a method for examining a sample (9) by means of an endoscopic system (8).

15 Claims, 8 Drawing Sheets

(56) References Cited

U.S. PATENT DOCUMENTS

| | | | |
|---|---|---|---|
| 2008/0304074 A1* | 12/2008 | Brennan, III | G01B 9/0203 356/451 |
| 2010/0046897 A1 | 2/2010 | Toriya et al. | |
| 2010/0329671 A1* | 12/2010 | Essiambre | H04B 10/2581 398/44 |
| 2011/0268141 A1 | 11/2011 | Nakatate | |
| 2017/0100024 A1* | 4/2017 | Shahmoon | G02B 6/02042 |
| 2019/0212761 A1* | 7/2019 | Swanson | A61B 5/0075 |
| 2019/0270667 A1 | 9/2019 | Sumita et al. | |
| 2020/0174181 A1 | 6/2020 | Shahmoon et al. | |
| 2020/0326472 A1* | 10/2020 | Li | G02B 6/02042 |
| 2020/0348505 A1 | 11/2020 | Gopinath et al. | |
| 2021/0215535 A1* | 7/2021 | Matz | A61B 1/00172 |

OTHER PUBLICATIONS

German Patent and Trademark Office, Office Action issued in related Application No. 10 2021102 092.1 dated Jun. 30, 2021, 14 pages.

German Patent and Trademark Office, Summons to Attend Oral Proceedings issued in related Application No. 10 2021102 092.1 dated Jul. 16, 2024, 13 pages.

* cited by examiner

HYBRID OPTICAL FIBER, ENDOSCOPIC SYSTEM, AND METHOD FOR EXAMINING A SAMPLE

CROSS REFERENCE TO RELATED APPLICATION(S)

This application relates to, and claims the benefit and priority from International Patent Application No PCT/EP2022/052052 filed Jan. 28, 2022 that published as International Patent Publication No. WO 2022/162147 on Aug. 4, 2022, which claims the benefit and priority from German Patent Application No. 10 2021 102 092. 1 filed on Jan. 29, 2021, the entire disclosures of which are incorporated herein by reference.

FIELD OF THE INVENTION

The invention relates to a hybrid optical fiber, to an endoscopic system for examining a sample and to a method for examining a sample by means of an endoscopic system.

BACKGROUND

Endoscopic methods are used in a wide variety of embodiments and for examining a wide variety of samples. One class of endoscopic methods is based on the use of optical fibers as probes. As a result of the usually relatively small diameter of these optical fibers, these endoscopic methods are only minimally invasive.

As an example, mention is made of the endoscopy using fiber bundles or using what are known as multicore optical fibers. In the case of fiber bundles, a plurality of optical fibers with one or a few excitable light modes are combined to form a bundle. By contrast, in the case of multicore optical fibers, a plurality of fiber cores with one or a few excitable light modes are combined within an overall cladding. Each individual optical fiber or each individual fiber core serves as an individual image pixel, such that the achievable resolution is dependent on the spacing between the individual optical fibers or fiber cores.

As a further example, mention is made of holographic endoscopy, that is to say the endoscopy using an endoscopic system with a multimode optical fiber as probe. This type of endoscopy offers the possibility of obtaining particularly high-resolution images of samples. This method has the disadvantage that it can only be utilized in the case of motionless samples, since precise manipulation of the wavefront has to be ensured and the latter is very sensitive to bending or deformation of the multimode optical fibers.

SUMMARY

It is therefore the object of the invention to propose an endoscopic system, a probe belonging to the endoscopic system and a method for examining a sample which overcome the aforementioned disadvantages of the prior art, thus in particular provide a particularly high resolution and are able to be utilized in the case of moving samples. This object is achieved by the subject matter of the independent patent claims. Refinements of the invention emerge from the dependent claims and from the following description.

One aspect of the invention relates to a hybrid optical fiber which comprises a plurality of fiber cores. In this case, the fiber cores are configured in such a way that one or a few light modes can be excited for the light to be used, in particular in the range of the visible spectrum, that is to say with wavelengths in the range from about 380 nm to 750 nm.

Furthermore, the hybrid optical fiber comprises a first cladding which encloses the plurality of fiber cores. In a cross section of the hybrid optical fiber, the first cladding is in particular of circular form and the plurality of fiber cores are arranged within the first cladding.

The hybrid optical fiber further comprises a second cladding which surrounds the first cladding. In a cross section of the hybrid optical fiber, the second cladding is in particular of annular form, the inner side of the second cladding corresponding to the outer side of the first cladding.

The fiber cores have a first refractive index $n_1$, the first cladding has a second refractive index $n_2$ and the second cladding has a third refractive index $n_3$. In this case, $n_1$ is greater than $n_2$ and $n_2$ is greater than $n_3$. Due to the fact that $n_1$ is greater than $n_2$, total reflection in the individual fiber cores is enabled, such that optical waveguiding can take place within the individual fiber cores. Due to the fact that $n_2$ is greater than $n_3$, total reflection at the boundary between the first cladding and the second cladding is also enabled, such that the first cladding together with the fiber cores can function as a multimode optical fiber.

It is thus possible for the first cladding to be used together with the plurality of fiber cores as a multimode optical fiber. In this way, it is possible, by means of a corresponding endoscopic system, to examine in particular a motionless sample with high resolution.

It is alternatively possible for the individual fiber cores to be used to examine the sample, each fiber core then corresponding to an image pixel. In this case, the examination of a moving sample is also possible, since there is a virtual insensitivity to bending or deformation of the fiber cores during the excitation of the fiber cores with one or a few light modes.

The hybrid optical fiber thus offers both the possibility of examining a motionless sample with high resolution and the possibility of examining a moving sample, the resolution then being limited to the spacing between the fiber cores.

In some embodiments, the fiber cores are arranged in an orthogonal point group or in a hexagonal point group in a cross section of the hybrid optical fiber. The arrangement in an orthogonal point group means that the fiber cores are arranged at the intersection points of a rectangular grid. In particular, the fiber cores may be arranged at the intersection points of a square grid. This results in a particularly simple arrangement of the fiber cores in an orthogonal coordinate system. By contrast, the arrangement in a hexagonal point group means that the fiber cores are arranged at the intersection points of a hexagonal grid. This arrangement corresponds to the densest packing of the fiber cores in the hybrid optical fiber, such that a maximum number of fiber cores with a predefined diameter can be arranged in a first cladding with a predefined diameter. It should be noted here that the fiber cores usually do not touch in a cross section of the hybrid optical fiber, such that the light mode or light modes excited in the fiber core are not coupled into adjacent fiber cores. A predefined minimum spacing between two fiber cores is thus observed, as seen in cross section. Furthermore, non-ordered and/or chaotic arrangements of the fiber cores are for example also conceivable.

In some embodiments, a diameter of the fiber cores is between 5 μm and 20 μm, in particular between 8 μm and 13 μm. With these diameters, it is possible for one to a few light modes to be excited in the fiber core and for good resolutions, up to about 10 μm, to be achieved.

In some embodiments, a spacing between two adjacent fiber cores is between 10 μm and 50 μm, in particular between 20 μm and 30 μm. This spacing, together with a corresponding diameter of the fiber cores, ensures that coupling of the light modes from one fiber core to an adjacent fiber core cannot take place and the individual fiber cores can thus function as individual image pixels.

In some embodiments, the number of fiber cores in the hybrid optical fiber is between 30 and 100, in particular between 50 and 70. With this number of fiber cores, a course image of the sample can be obtained, particularly if the sample is moving, at the same time a diameter of the hybrid optical fiber remains relatively small, such that the sample is not damaged too greatly by the hybrid optical fiber.

In some embodiments, the hybrid optical fiber further comprises a protective coating and/or outer jacket surrounding the second cladding. The second cladding is thus protected against external influences and the service life of the hybrid optical fiber is extended.

A further aspect of the invention relates to an endoscopic system for examining a sample. In this case, the sample may be immobile or largely immobile at a first point in time and be mobile at a second point in time. In particular, the sample is an animal, more particularly a human. With the aid of the endoscopic system, it is for example possible in this case to examine neurons and/or the networking of neurons in the sample.

The endoscopic system comprises a hybrid optical fiber according to the preceding description.

Furthermore, the endoscopic system comprises an optical arrangement. The optical arrangement comprises a coherent light source for introducing light into a proximal end of the hybrid optical fiber. The coherent light source may for example be a laser, wherein the light wavefront emitted by the laser is modified by means of a modifier. In this case, the light from the coherent light source may be introduced into the proximal end of the hybrid optical fiber in such a way that the fiber cores of the hybrid optical fiber together with the first cladding of the hybrid optical fiber function as a multimode optical fiber. Furthermore, the optical arrangement comprises a photodetector, comprising a plurality of pixels, for detecting the light exiting the individual fiber cores. In this case, this light is emitted by the object point or region illuminated by the light in front of the distal end of the hybrid optical fiber. This light response may for example be effected by reflection, fluorescence, Raman scattering, stimulated Raman scattering, coherent anti-Stokes Raman scattering, autofluorescence and/or frequency doubling. The light emitted by the illuminated object point or region is conducted by the individual fiber cores and/or the first cladding to the proximal end of the hybrid optical fiber. In order for the illumination and detection to be able to be effected at the same time, the coherent light source and the photodetector are incorporated into the optical arrangement for example by way of a beam splitter, in particular by way of a dichroic beam splitter.

In some embodiments, the endoscopic system is configured to be operated in a first operating mode and in a second operating mode. In the first operating mode, light modes in the hybrid optical fiber functioning as a multimode optical fiber are excited by means of the coherent light source in such a way that individual object points in the sample are successively illuminated. The light response emitted by the individual object points is detected by the photodetector. Here, summing is performed in particular over all pixels of the photodetector. In the first operating mode, which is preferably used in the case of a motionless sample, an examination of the sample with a particularly high resolution can thus be obtained.

In the second operating mode, objects in the sample are illuminated by means of the coherent light source. In this case, the light response emitted by the objects is detected separately for each fiber core by the photodetector. To this end, each fiber core is assigned at least one pixel of the second photodetector. In the second operating mode, moving samples can also be examined, the resolution being limited to the spacing between two fiber cores.

In some embodiments, the optical arrangement comprises a further light source for introducing light into the fiber cores and/or into the first cladding. In this case, the further light source preferably comprises a plurality of partial light sources. These partial light sources may in particular be LEDs. In this case, the partial light sources are preferably arranged in an array, such that the partial light sources are assigned to the fiber cores of the hybrid optical fiber. Light is thus introduced separately into each fiber core. In this case, it is possible to introduce light simultaneously into all the fiber cores or to introduce light successively into the individual fiber cores. The further light source is preferably used to illuminate the objects of the sample in the second operating mode of the endoscopic system.

In some embodiments, the optical arrangement comprises a further photodetector for detecting the light exiting the fiber cores and the first cladding. The coherent light source and the further photodetector are in this case assigned to a first optical partial arrangement, while the further light source and the photodetector are assigned to a second optical partial arrangement. Preferably, the first operating mode is carried out by means of the first optical partial arrangement and the second operating mode is carried out by means of the second optical partial arrangement.

In some embodiments, the endoscopic system further comprises a switching device for changing between the first optical partial arrangement and the second optical partial arrangement. The switching device may, for example, be of optical configuration, e.g. by way of an adjustable mirror, or of mechanical configuration, by displacement of the first and second optical partial arrangement. The switching device can thus be used to change between the high-resolution examination of the motionless sample by means of the first optical partial arrangement and the lower-resolution examination of the moving sample by means of the second optical partial arrangement.

In some embodiments, the first optical partial arrangement and/or the second optical partial arrangement can be used separately with the hybrid optical fiber. In these cases, it is thus possible for the respectively other optical partial arrangement to be separated from the rest of the endoscopic system. This is of particular interest when the first optical partial arrangement, which owing to the coherent light source is usually very large in comparison with the second optical partial arrangement, is separated from the rest of the endoscopic system and the hybrid optical fiber remains with the comparatively small second optical partial arrangement for examination of the moving sample.

In some embodiments, the hybrid optical fiber is composed of at least a first part and a second part. In this case, the first part and the second part are connected to one another in a separable manner by way of a connecting element. For this purpose, for example at that end of the first part which faces the second part and at that end of the second part which faces the first part, ceramic end sleeves are fitted to the first and/or second part of the hybrid optical fiber. The two parts are then connected to one another by way of a connecting sleeve. The first part, which is introduced into the sample, can thus remain in the sample and the rest of the endoscopic system can be connected to the first part by means of the second part for an examination.

In some embodiments, the optical arrangement in the first operating mode and/or the first optical partial arrangement have/has a first numerical aperture $NA_1$, and the optical arrangement in the second operating mode and/or the second optical partial arrangement have/has a second numerical aperture $NA_2$, $NA_1$ being greater than $NA_2$. $NA_1$ is so great that the light coupled into the fiber cores and into the first cladding can pass from the fiber cores to the first cladding and back, such that the fiber cores and the first cladding together can function as multimode optical fibers. By contrast, $NA_2$ is so small that light cannot pass from the fiber cores into the cladding, such that the light remains in the individual fiber cores and each fiber core can function as an individual pixel.

A further aspect of the invention relates to a method for examining a sample. The sample may initially be immobile or largely immobile and be mobile at a later point in time. In particular, the sample is an animal, more particularly a human. With the aid of the endoscopic system, it is for example possible in this case to examine neurons and/or the networking of neurons in the sample.

The method is carried out by means of an endoscopic system according to the preceding description. In this case, the hybrid optical fiber of the endoscopic system is introduced into the sample.

Initially, the sample is immobile and the optical arrangement and/or the first optical partial arrangement of the endoscopic system are/is connected to the hybrid optical fiber. Light is introduced into the fiber cores and the first cladding of the hybrid optical fiber by means of the coherent light source, such that the hybrid optical fiber functions as a multimode optical fiber. A multiplicity of object points in the sample are successively illuminated by the hybrid optical fiber and the light response emitted by the object points is detected through the hybrid optical fiber and by means of the photodetector or further photodetector. This examination of the motionless sample provides images with a particularly high resolution.

At a later point in time, the sample is moving and the optical arrangement and/or the second optical partial arrangement of the endoscopic system are/is connected to the hybrid optical fiber. Light is introduced into the fiber cores and/or into the first cladding by means of the coherent light source or the further light source. As a result, objects at distal ends of the fiber cores are illuminated. The light response emitted by the objects is conducted through the fiber cores to the photodetector and is detected by pixels of the photodetector. Although this examination provides images with a lower resolution, it can be performed on the moving sample.

Since the examinations with the high resolution on the motionless sample and with the lower resolution on the moving sample are performed with the same hybrid optical fiber, precise assignment of the pixels obtained by way of the fiber cores to regions in the high-resolution image is possible.

In some embodiments, light transmission properties of the hybrid optical fiber in the use as multimode optical fiber are measured prior to the examination of the sample. In this case, the hybrid optical fiber is preferably kept in the shape, for example rectilinear or with curvatures, in which it then also comes to lie in the sample. Defined coherent light is introduced into the hybrid optical fiber on one side of the hybrid optical fiber and the result is measured on the other side of the hybrid optical fiber. It is thus possible to ascertain which modifications to the coherent light are required to obtain the illumination of an individual object point.

As an alternative or in addition to the measurement of the light transmission properties, the light transmission properties of the hybrid optical fiber may also be calculated by a modeling based on the wave propagation.

In some embodiments, when the second optical partial arrangement is connected to the hybrid optical fiber, the first optical partial arrangement is completely separated from the hybrid optical fiber. This separation can be effected mechanically in various ways. As a result of the separation of the first optical partial arrangement, which is very large in comparison with the second optical partial arrangement, only the smaller second optical partial arrangement remains connected to the hybrid optical fiber and thus to the sample during the examination of the moving sample. This enables an easier examination of the sample, for example in that the second optical partial arrangement is fastened to the sample.

In some embodiments, after an examination of the sample, the hybrid optical fiber is separated into a first part, which is inserted into the sample, and a second part. The first part of the hybrid optical fiber thus remains in the sample, but due to its small dimensions and its low weight has only a small disturbing effect, if any, on the sample. At a later point in time, the first part and the second part are connected to one another again for a further examination of the sample. In this way, firstly, a reintroduction of the hybrid optical fiber into the sample is omitted, and, secondly, precisely the same location of the sample as in the first examination is examined again.

It goes without saying that a preferred embodiment may also be obtained from a combination of dependent claims with the respective independent claim.

For further elucidation, the invention will be described on the basis of embodiments depicted in the figures. These embodiments should be understood merely as examples and not as limitations.

BRIEF DESCRIPTION OF THE FIGURES

In the figures:

FIG. 6b shows a further schematic view of the exemplary embodiment of the endoscopic system from FIG. 6a.

DETAILED DESCRIPTION OF EMBODIMENTS

In the figures, identical reference signs denote either identical elements or elements with equivalent functions. Elements which have already been described are not necessarily described again in subsequent figures.

Figure 1:
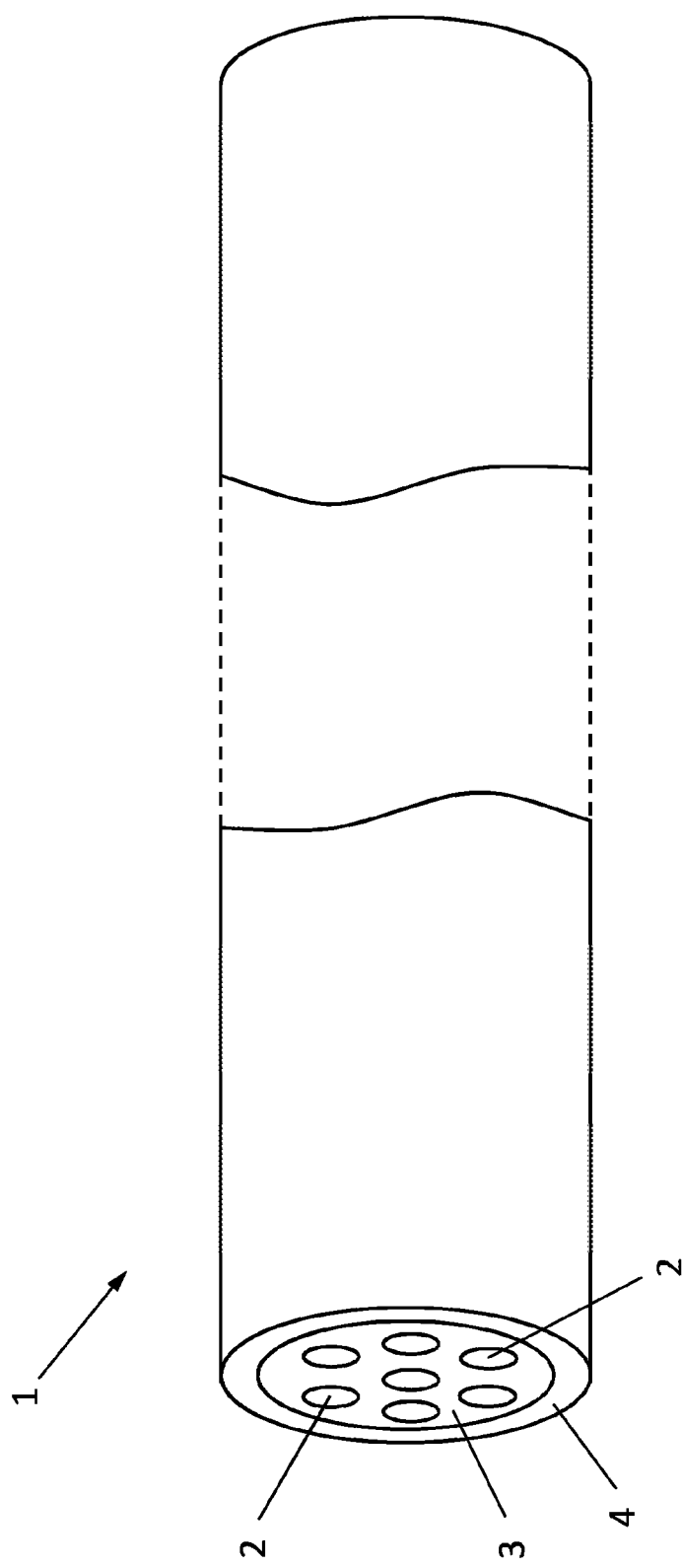
FIG. 1 shows a perspective view of an exemplary embodiment of a hybrid optical fiber.

FIG. 1 shows a perspective view of an exemplary embodiment of a hybrid optical fiber 1. The hybrid optical fiber 1 comprises a plurality of fiber cores 2. These fiber cores 2 are enclosed by a common first cladding 3. In this case, a first refractive index ni of the fiber cores 2 is greater than a second refractive index nz of the first cladding 3, such that light running in the fiber cores 2 can undergo total reflection at the boundary surface between fiber core 2 and first cladding 3. In the case of a corresponding entrance angle of the light or in the case of a corresponding numerical aperture of an optical arrangement connected to the hybrid optical fiber 1, the fiber cores 2 can thus be referred to as individual optical fibers.

A second cladding 4 is also arranged so as to surround the first cladding 3. In this case, the second refractive index nz of the first cladding 3 is greater than a third refractive index n 3 of the second cladding 4, such that light running in the first cladding 3 can undergo total reflection at the boundary surface between first cladding 3 and second cladding 4. In the case of a corresponding entrance angle of the light or in the case of a corresponding numerical aperture of an optical arrangement connected to the hybrid optical fiber 1, the fiber cores 2 together with the first cladding 3 can thus function as a multimode optical fiber, the light undergoing total reflection at the boundary surface between first cladding 3 and second cladding 4.

Depending on the numerical aperture of the optical arrangement connected to the hybrid optical fiber 1, two different operating modes of the hybrid optical fiber 1 are thus possible: firstly, the fiber cores 2 together with the first cladding 3 can function as a multimode optical fiber, as a result of which a particularly high resolution is enabled. Since, however, the propagation of the many light modes in the multimode optical fiber is sensitive to deformations and bending of the optical fiber, this operating mode is limited to predominantly immobile samples. In the second operating mode, the individual fiber cores 2 function as optical fibers, only one or a few light modes being excited in each case. Although the resolution is limited to the spacing between the individual fiber cores 2 in this operating mode, it also allows examinations on moving samples to be performed.

Mention is made as an example here of the examination of neurons and of the networking of neurons in the brain of an animal or a human. First, the hybrid optical fiber 1 is introduced into the brain of the sedated animal or human. In the sedated state, high-resolution images are then also already taken with the hybrid optical fiber 1 as multimode optical fiber. These images show, by way of example, individual neurons and the networking between these neurons. During the further course of the examination, the animal or the human is brought into the awake state. In the awake state, images are then taken with the individual fiber cores 2 as optical fibers, it being possible here to observe for example the individual neurons, but no longer the networking between the neurons. Since the same hybrid optical fiber 1 is used for both images and its position is not changed between the images, it is possible for the neurons observed by means of the individual fiber cores 2 to be assigned to the neurons from the high- resolution image.

Figure 2:
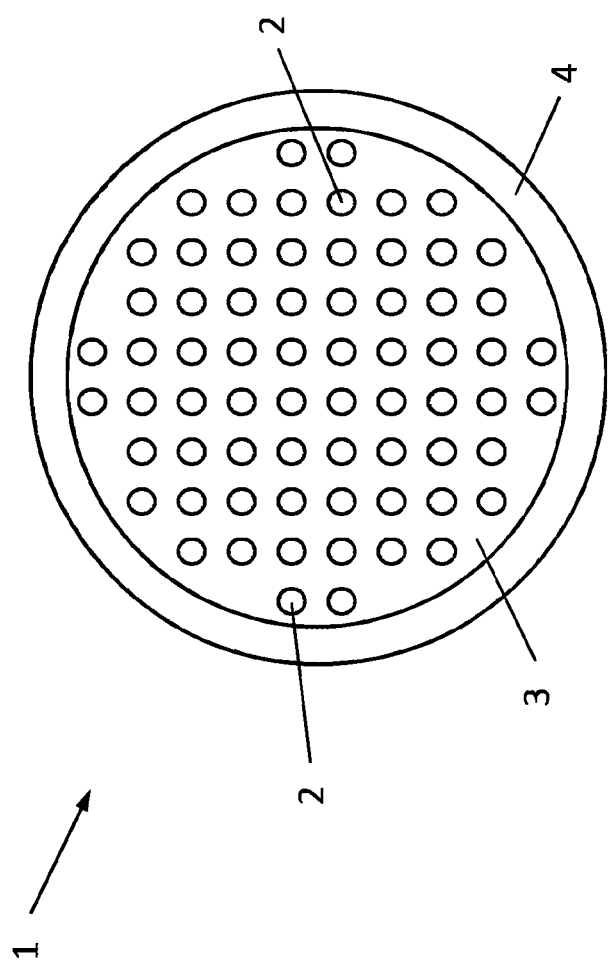
FIG. 2 shows a cross section through a further exemplary embodiment of a hybrid optical fiber.

FIG. 2 shows a cross section through a further exemplary embodiment of a hybrid optical fiber 1. In this exemplary embodiment, a multiplicity of fiber cores 2 are arranged in an orthogonal point group. Imaging in an orthogonal coordinate system is particularly simple with this arrangement of the fiber cores 2.

Figure 3:
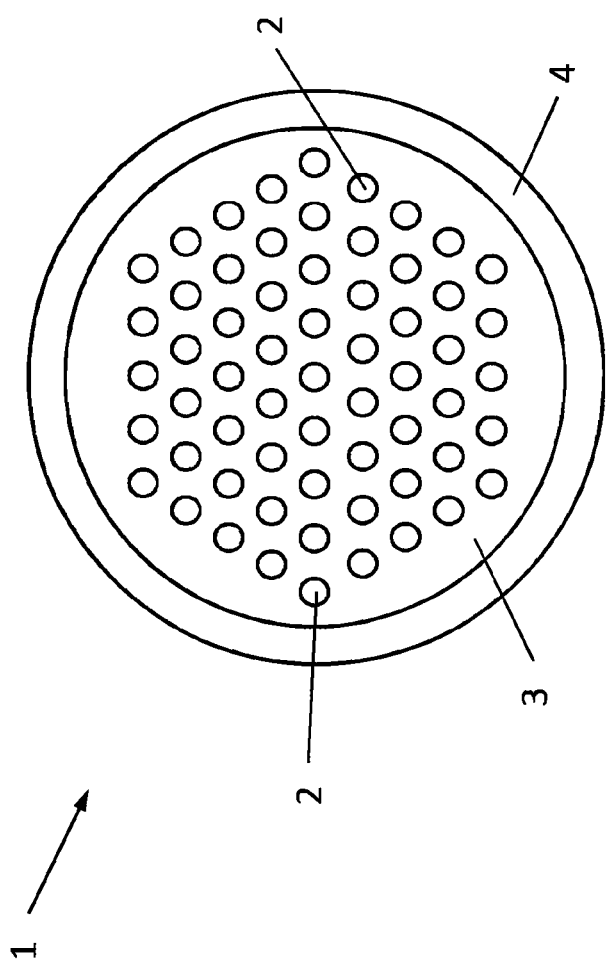
FIG. 3 shows a cross section through yet a further exemplary embodiment of a hybrid optical fiber.

FIG. 3 shows a cross section through yet a further exemplary embodiment of a hybrid optical fiber 1. In this exemplary embodiment, the fiber cores 2 are arranged in a hexagonal point group. It is thus possible, with a given spacing between adjacent fiber cores 2, to arrange the largest possible number of fiber cores 2 within the first cladding 3. Furthermore, the arrangement of the fiber cores 2 in the hexagonal point group provides a particularly good stability of the hybrid optical fiber 1.

Figure 4:
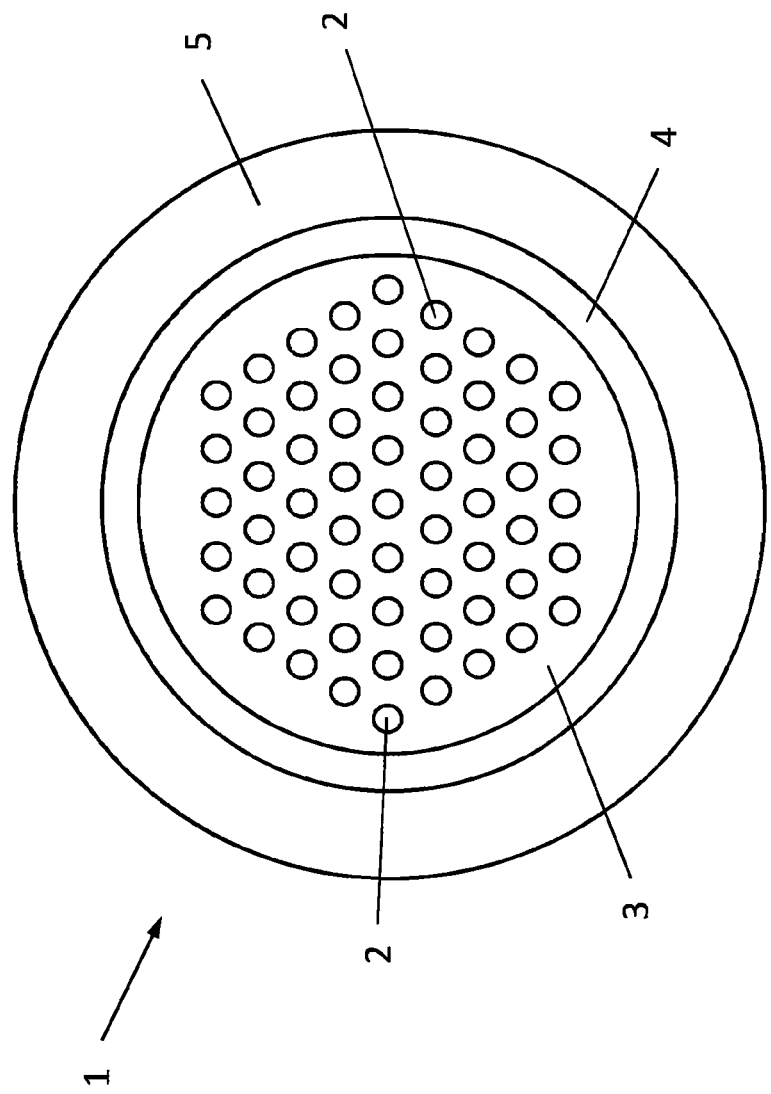
FIG. 4 shows a cross section through yet a further exemplary embodiment of a hybrid optical fiber.

FIG. 4 shows a cross section through yet a further exemplary embodiment of a hybrid optical fiber 1. In this exemplary embodiment, a protective coating 5 which surrounds the second cladding 4 is arranged around the second cladding 4. This protective coating 5 protects the hybrid optical fiber 1 against external influences, for example against chemical or physical influences.

Figure 5:
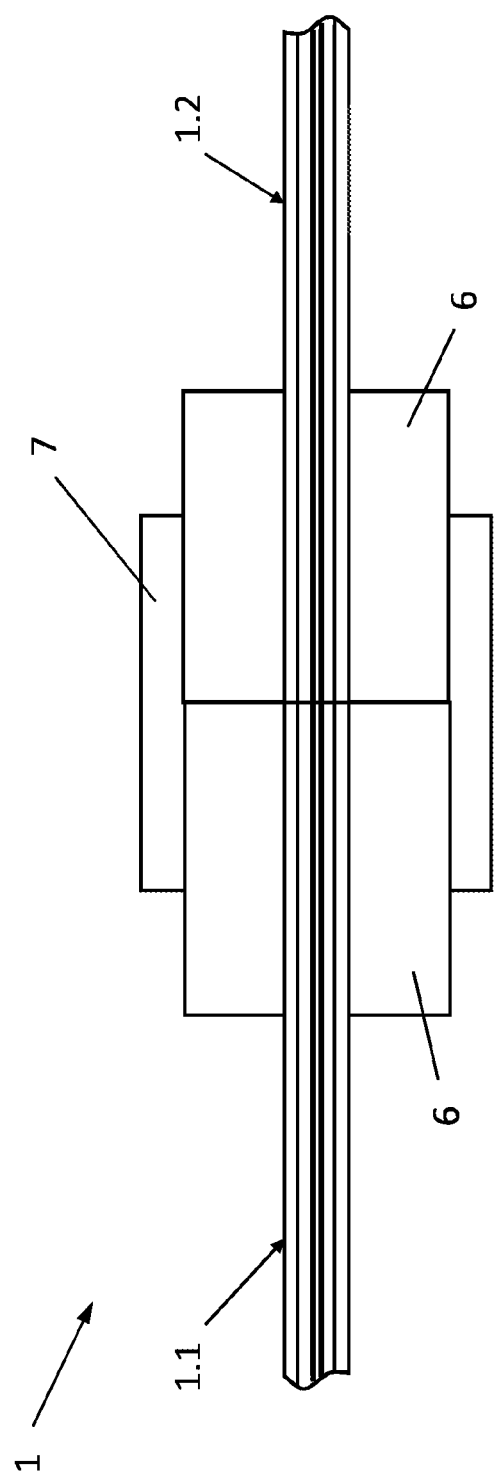
FIG. 5 shows a longitudinal section through an assembled first part and second part of a hybrid optical fiber.

FIG. 5 shows a detail of a longitudinal section through a further exemplary embodiment of a hybrid optical fiber 1. This hybrid optical fiber 1 is composed of a first part 1.1 and a second part 1.2. In order to connect the first part 1.1 to the second part 1.2, ceramic end sleeves 6 are fitted on that end of the first part 1.1 which faces the second part 1.2 and on that end of the second part 1.2 which faces the first part 1.1. An inner diameter of the ceramic end sleeves 6 corresponds in this case precisely to an outer diameter of the second cladding 4. The first part 1.1 is connected to the second part 1.2 by way of a connecting sleeve 7, into which the two ceramic end sleeves are plugged. Such a connection allows the first part 1.1 of the hybrid optical fiber 1 to be left in a sample while the second part 1.2 together with the rest of the endoscopic system is separated from the sample. The first part 1.1 has only a very minor adverse effect, if any, on the sample. For renewed examinations, the first part 1.1 and the second part 1.2 are then connected to one another again.

Figure 6A:
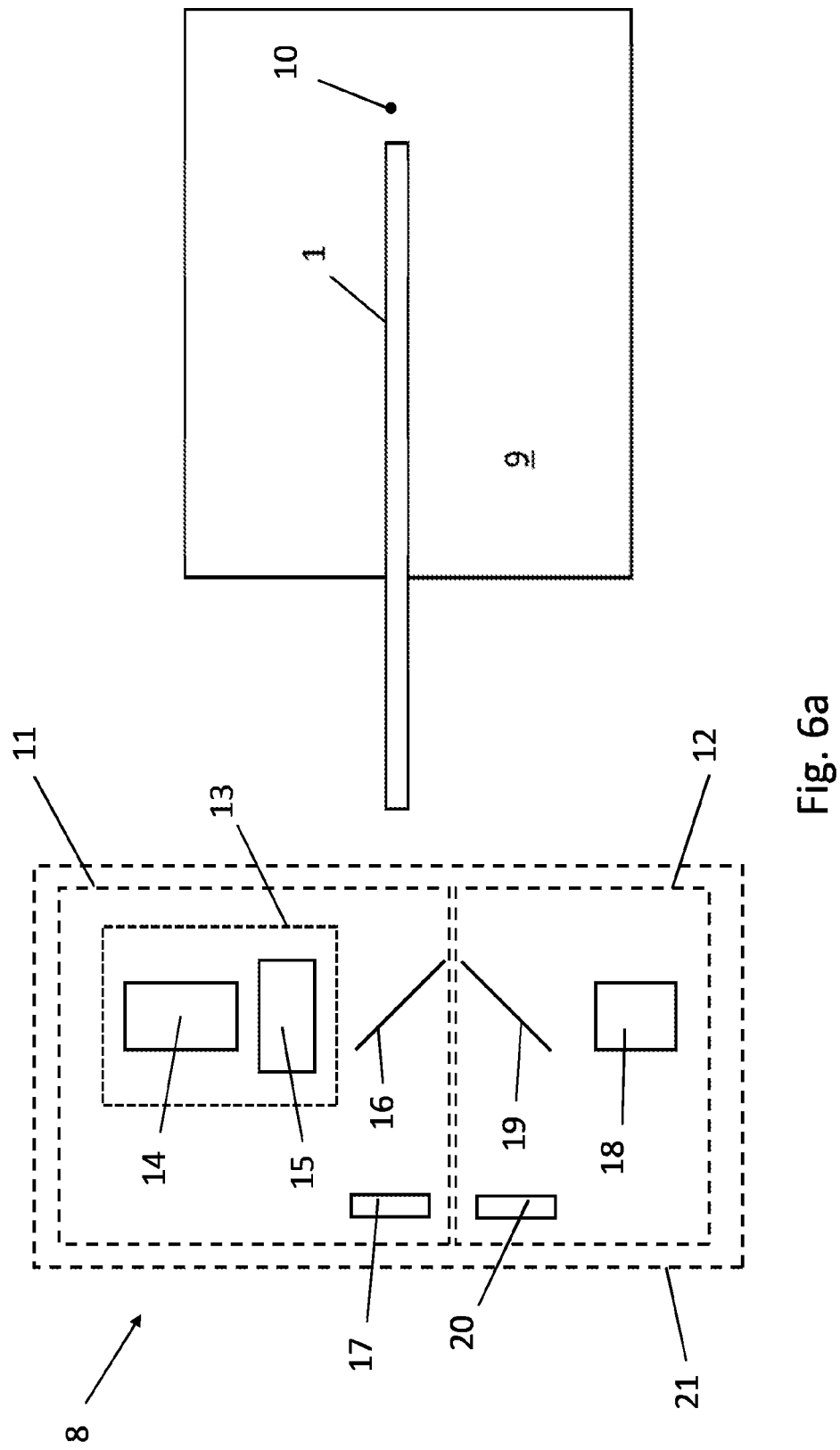
FIG. 6a shows a schematic view of an exemplary embodiment of an endoscopic system.

FIG. 6a shows a schematic view of an exemplary embodiment of an endoscopic system 8. A hybrid optical fiber 1 is introduced into a sample 9 in order to examine objects 10 in front of the hybrid optical fiber 1.

The endoscopic system 8 comprises an optical arrangement 21 which comprises a first optical partial arrangement 11 and a second optical partial arrangement 12. A mechanical system, which is not illustrated in any more detail here, can be used to couple either the first optical partial arrangement 11 or the second optical partial arrangement 12 to the hybrid optical fiber 1. In this case, the first optical partial arrangement 11 is coupled to the hybrid optical fiber 1 in FIG. 6a. As an alternative thereto, it is possible to perform the change between the first optical partial arrangement 11 and the second optical partial arrangement 12 by way of optical elements, for example an adjustable mirror. Furthermore, it is also possible for only the first optical partial arrangement 11 or the second optical partial arrangement 12 to be connected to the hybrid optical fiber 1 at a given point in time, while the respectively other optical partial arrangement 12 or 11 is separated from the hybrid optical fiber 1.

The first optical partial arrangement 11 comprises a coherent light source 13 comprising a laser 14 and a modifier 15 which modifies the light wavefront emitted by the laser 14. A first beam splitter 16, which is for example a dichroic beam splitter, is used to optically connect the coherent light source 13 to the hybrid optical fiber 1, the fiber cores 2 together with the first cladding 3 functioning as a multimode optical fiber. In the case of an examination of the sample 9, the coherent light of the laser 14 is modified by means of the modifier 15 in such a way that in each case only one point of the object 10 is illuminated. The necessary knowledge of the light transmission properties of the hybrid optical fiber 1 are, to this end, measured and/or calculated prior to the examination. The light response emitted by the illuminated point of the object 10 for example by reflection, fluorescence, Raman scattering, stimulated Raman scattering, coherent anti-Stokes Raman scattering, autofluorescence and/or frequency doubling is conducted by the hybrid optical fiber 1 out of the sample 9 and passes via the first beam splitter 16 to a further photodetector 17 of the first optical partial arrangement 11, where said light response is detected. By virtue of a multiplicity of points of the object 10 being successively illuminated, a high-resolution image can be created.

Figure 6B:
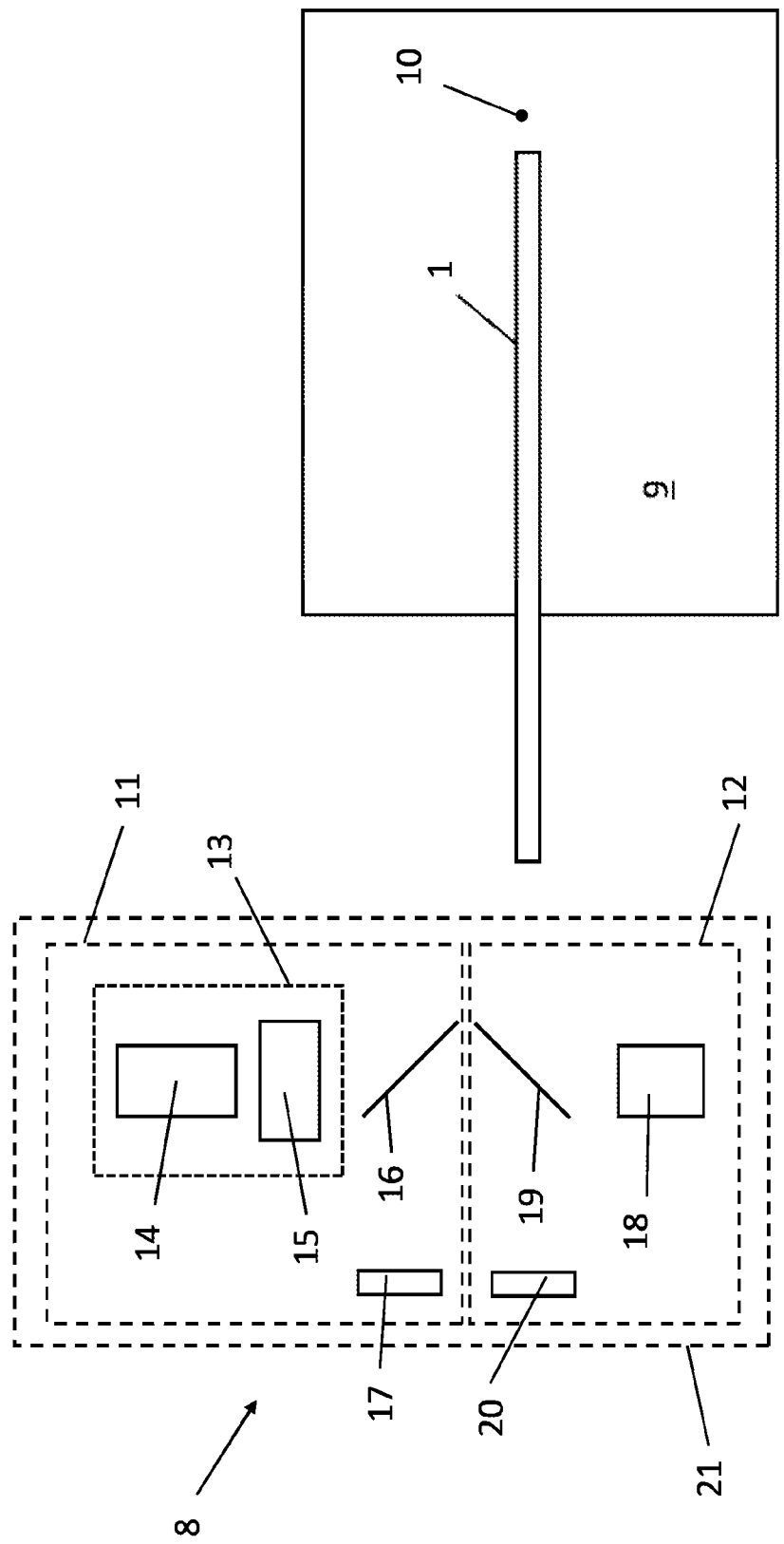

FIG. 6b shows the endoscopic system 8 from FIG. 6a again, the second optical partial arrangement 12 having been coupled to the hybrid optical fiber 1 by means of the mechanical system. The second optical partial arrangement 12 comprises a further light source 18 which introduces light into the fiber cores 2 and/or into the first cladding 3. In this case, the further light source 18 comprises, for example, an array of LEDs, each fiber core 2 being assigned an LED. The light from the further light source 18 illuminates the object 10 via a second beam splitter 19, which is for example a dichroic beam splitter, and the hybrid optical fiber 1. A light response emitted by the object 10 for example by reflection, fluorescence, Raman scattering, stimulated Raman scattering, coherent anti-Stokes Raman scattering, autofluorescence and/or frequency doubling then passes via the fiber cores 2 of the hybrid optical fiber 1 and the second beam splitter 19 to a photodetector 20 of the second optical partial arrangement 12. The photodetector 20 in this case comprises a plurality of pixels for detecting the light exiting the individual fiber cores 2. The resolution of the combination of the hybrid optical fiber 1 with the second optical arrangement 12 is limited to the spacing between the fiber cores 2, however examinations on a moving sample 9 can also be performed with this combination.

Figure 7:
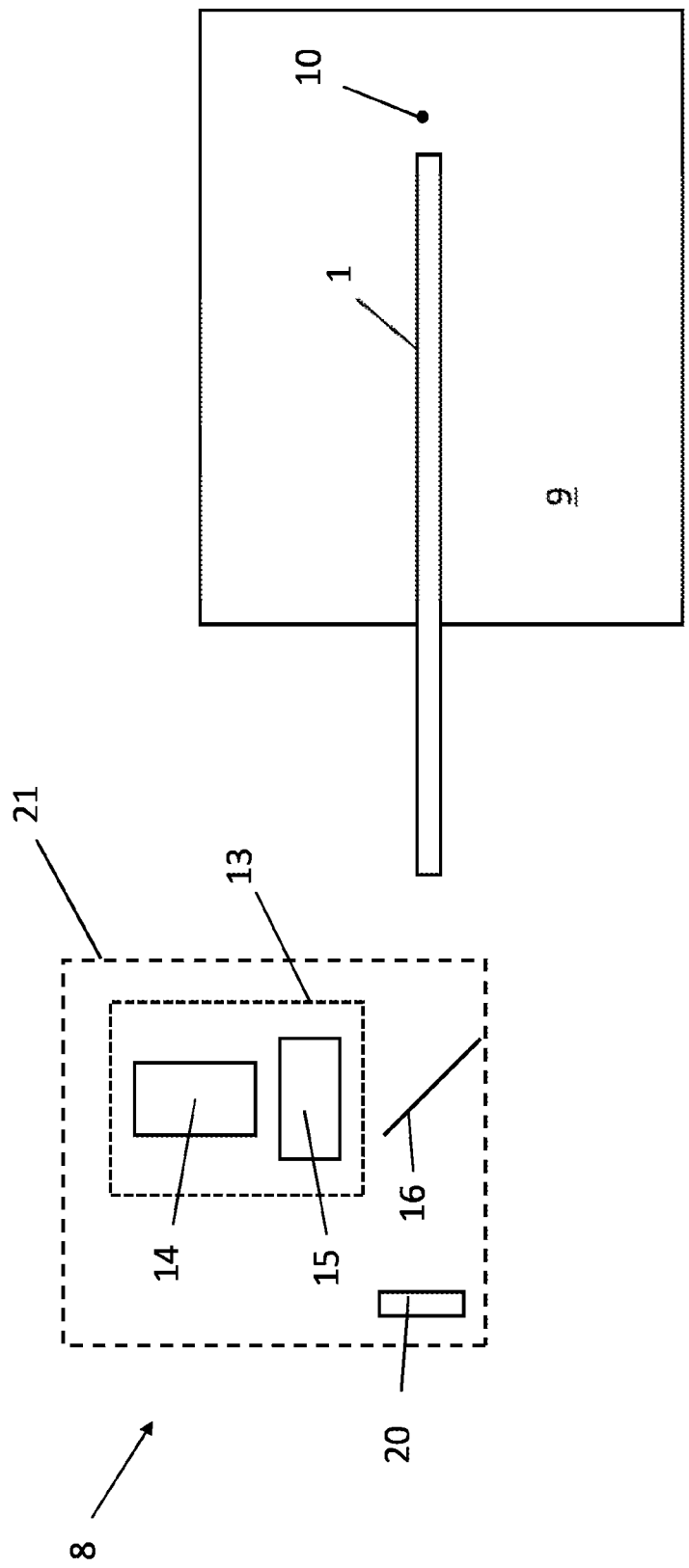
FIG. 7 shows a schematic view of a further exemplary embodiment of an endoscopic system.

FIG. 7 shows a schematic view of a further exemplary embodiment of an endoscopic system 8. The optical arrangement 21 of this endoscopic system 8 comprises merely a coherent light source 13 and a photodetector 20. In this case, the coherent light source 13 introduces the light into the hybrid optical fiber 1 both in a first operating mode and in a second operating mode of the endoscopic system 8. In the first operating mode, the light modes in the hybrid optical fiber 1 functioning as a multimode optical fiber are excited in such a way that individual object points in the sample 9 are successively illuminated. In the second operating mode, objects in the sample 9 are illuminated by means of the coherent light source 13. Equally, the light response of the object points or objects is detected by the photodetector 20 both in the first and in the second operating mode. In this case, summing is performed over all pixels of the photodetector 20 in the first operating mode, while the light response is detected separately for each fiber core 2 in the second operating mode.

The invention claimed is:

1. An endoscopic system for examining a sample, comprising:
   a hybrid optical fiber comprising:
      a plurality of fiber cores,
      a first cladding enclosing the plurality of fiber cores, and
      a second cladding enclosing the first cladding, wherein the plurality of fiber cores have a first refractive index, the first cladding has a second refractive index and the second cladding has a third refractive index, wherein the first refractive index is greater than second refractive index, and the second refractive index is greater than the third refractive index; and
   an optical arrangement comprising:
      a coherent light source configured to introduce light into a proximal end of the hybrid optical fiber such that the plurality of fiber cores and the first cladding function as a multimode optical fiber, and
      a photodetector comprising a plurality of pixels configured to detect the light emerging from individual ones of the plurality of fiber cores,
   wherein the optical arrangement is configured such that, in operation, upon the light being provided to the hybrid optical fiber and the first cladding, the light is completely reflected at an interface between the first cladding and the second cladding.

2. The endoscopic system according to claim 1, wherein the optical arrangement comprises a further light source configured to introduce further light into at least one of the plurality of fiber cores or the first cladding.

3. An endoscopic system for examining a sample, comprising:
   a hybrid optical fiber comprising:
      a plurality of fiber cores,
      a first cladding enclosing the plurality of fiber cores, and
      a second cladding enclosing the first cladding, wherein the plurality of fiber cores have a first refractive index, the first cladding has a second refractive index and the second cladding has a third refractive index, wherein the first refractive index is greater than second refractive index, and the second refractive index is greater than the third refractive index; and
   an optical arrangement comprising:
      a coherent light source configured to introduce light into a proximal end of the hybrid optical fiber such that the plurality of fiber cores and the first cladding function as a multimode optical fiber, and
      a photodetector comprising a plurality of pixels configured to detect the light emerging from individual ones of the plurality of fiber cores,
   wherein the endoscopic system is further adapted to operate in:
      a first operating mode in which the coherent light source is used to excite light modes in the hybrid optical fiber functioning as the multimode optical fiber in such a way that individual object points in the sample are illuminated one after another, and the light response emitted by the object points is detected by the photodetector, and
      a second operating mode in which the coherent light source is used to illuminate objects in the sample, and the light response emitted by the objects is detected separately for each of the plurality of fiber cores by the photodetector.

4. The endoscopic system according to claim 3, wherein the light response emitted by the object points is detected as a sum over all pixels.

5. The endoscopic system according to claim 3,
   wherein the optical arrangement comprises a further light source configured to introduce further light into at least one of the plurality of fiber cores or the first cladding,
   wherein the further light source has a plurality of partial light sources, and wherein the partial light sources are arranged in an array and assigned to the plurality of fiber cores of the hybrid optical fiber, and wherein the objects in the sample are illuminated by the additional light source,
   wherein the optical arrangement comprises a further photodetector configured to detect the light or the further light emerging from the plurality of fiber cores and the first cladding, wherein the coherent light source and the further photodetector are assigned to a first optical subassembly, wherein the further light source and the photodetector are assigned to a second optical subassembly, wherein the optical arrangement comprises a further photodetector configured to detect the light or the further light emerging from the plurality of fiber cores and the first cladding, wherein the coherent light source and the further photodetector are assigned to a first optical subassembly, wherein the further light source and the photodetector are assigned to a second optical subassembly, and wherein the first operating mode is performed using the first optical part arrangement, and the second operating mode is performed using the second optical subassembly.

6. The endoscopic system according to claim 3, wherein at least one of (i) the optical arrangement in the first operating mode or (ii) a first optical subassembly has a first numerical aperture, and wherein at least one of (i) the optical arrangement in the second operating mode or (ii) a second optical subassembly has a second numerical aperture, and wherein the first numerical aperture is greater than the second numerical aperture.

7. An endoscopic system for examining a sample, comprising:
a hybrid optical fiber comprising:
a plurality of fiber cores,
a first cladding enclosing the plurality of fiber cores, and
a second cladding enclosing the first cladding, wherein the plurality of fiber cores have a first refractive index, the first cladding has a second refractive index and the second cladding has a third refractive index, wherein the first refractive index is greater than second refractive index, and the second refractive index is greater than the third refractive index; and
an optical arrangement comprising:
a coherent light source configured to introduce light into a proximal end of the hybrid optical fiber such that the plurality of fiber cores and the first cladding function as a multimode optical fiber, and
a photodetector comprising a plurality of pixels configured to detect the light emerging from individual ones of the plurality of fiber cores,
wherein the optical arrangement comprises a further light source configured to introduce further light into at least one of the plurality of fiber cores or the first cladding, and
wherein the further light source has a plurality of partial light sources, and wherein the partial light sources are arranged in an array and assigned to the plurality of fiber cores of the hybrid optical fiber, and wherein the objects in the sample are illuminated by the additional light source.

8. The endoscopic system according to claim 7, wherein the optical arrangement comprises a further photodetector configured to detect the light or the further light emerging from the plurality of fiber cores and the first cladding, wherein the coherent light source and the further photodetector are assigned to a first optical subassembly, wherein the further light source and the photodetector are assigned to a second optical subassembly.

9. The endoscopic system according to claim 8, further comprising a switching device configured to change between the first optical subassembly and the second optical subassembly.

10. The endoscopic system according to claim 8, wherein at least one of the first optical subassembly or the second optical subassembly is usable separately with the hybrid optical fiber.

11. An endoscopic system for examining a sample, comprising:
a hybrid optical fiber comprising:
a plurality of fiber cores,
a first cladding enclosing the plurality of fiber cores, and
a second cladding enclosing the first cladding, wherein the plurality of fiber cores have a first refractive index, the first cladding has a second refractive index and the second cladding has a third refractive index, wherein the first refractive index is greater than second refractive index, and the second refractive index is greater than the third refractive index; and
an optical arrangement comprising:
a coherent light source configured to introduce light into a proximal end of the hybrid optical fiber such that the plurality of fiber cores and the first cladding function as a multimode optical fiber, and
a photodetector comprising a plurality of pixels configured to detect the light emerging from individual ones of the plurality of fiber cores,
wherein the hybrid optical fiber includes a first part and a second part, and wherein the first part and the second part are connected to one another in a detachable manner via a connecting element.

12. A method for examining a sample using an endoscopic system which comprises a hybrid optical fiber comprising (i) a plurality of fiber cores, (ii) a first cladding enclosing the plurality of fiber cores, and (iii) a second cladding enclosing the first cladding, wherein the plurality of fiber cores have a first refractive index, the first cladding has a second refractive index and the second cladding has a third refractive index, wherein the first refractive index is greater than second refractive index, and the second refractive index is greater than the third refractive index, the endoscopic system further comprising an optical arrangement comprising (i) a coherent light source configured to introduce light into a proximal end of the hybrid optical fiber such that the plurality of fiber cores and the first cladding function as a multimode optical fiber, and (ii) a photodetector comprising a plurality of pixels configured to detect the light emerging from individual ones of the plurality of fiber cores, wherein the method comprising:
inserting the hybrid optical fiber of the endoscopic system into the sample which is initially immovable, wherein at least one of the optical arrangement or the first optical subassembly of the endoscopic system is connected to the hybrid optical fiber;
introducing light into the plurality of fiber cores and the first cladding of the hybrid optical fiber using the coherent light source, wherein the hybrid optical fiber functions as a multimode optical fiber, wherein a number of object points in the sample are illuminated one after another through the hybrid optical fiber; and
detecting the light response emitted by the object points via the hybrid optical fiber using the photodetector;
moving the sample, wherein the optical arrangement or the second optical subassembly of the endoscopic system is connected to the hybrid optical fiber;

introducing light into at least one of the plurality of fiber cores or the first cladding using the coherent light source or a further light source so as to illuminate objects at the distal ends of the fiber cores; and detecting a light response emitted from the objects which is passed through the plurality of fiber cores by the pixels of the photodetector.

13. The method according to claim 12, further comprising measuring or calculating light transmission properties of the hybrid optical fiber used as a multimode optical fiber before examining the sample.

14. The method according to claim 12, wherein, when the second optical subassembly is connected to the hybrid optical fiber, the first optical subassembly is completely disconnected from the hybrid optical fiber.

15. The method according to claim 12, further comprising after examining the sample, separating the hybrid optical fiber into a first part inserted into the sample and a second part; and reconnecting the first part and the second part to one another thereafter for a further examination of the sample.

\* \* \* \* \*